(12) United States Patent
Meyer

(10) Patent No.: US 6,500,136 B2
(45) Date of Patent: Dec. 31, 2002

(54) CERVICAL REMODELING COLLAR

(76) Inventor: Donald W. Meyer, 20254 Peach La., Huntington Beach, CA (US) 92646

(*) Notice: Subject to any disclaimer, the term of this patent is extended or adjusted under 35 U.S.C. 154(b) by 0 days.

(21) Appl. No.: 09/911,746

(22) Filed: Jul. 23, 2001

(65) Prior Publication Data

US 2001/0047143 A1 Nov. 29, 2001

Related U.S. Application Data

(63) Continuation of application No. 09/252,335, filed on Feb. 18, 1999, now abandoned.

(51) Int. Cl.⁷ .................................................. A61F 5/00
(52) U.S. Cl. ................................. 602/18; 602/17
(58) Field of Search ........................ 602/39, 40, 17–19, 602/32; 482/10, 11; 606/242; 128/DIG. 19

(56) References Cited

U.S. PATENT DOCUMENTS

| | | |
|---|---|---|
| 678,417 A | 7/1901 | Muller |
| 2,166,229 A | 7/1939 | Anderson |
| 2,815,022 A | 12/1957 | Krumm |
| 3,957,040 A | 5/1976 | Calabrese |
| 4,161,946 A | 7/1979 | Zuesse |
| 4,735,196 A | 4/1988 | Krag et al. |
| 4,951,655 A * | 8/1990 | MacMillian et al. ...... 128/76 R |
| 5,109,835 A | 5/1992 | McDonald et al. |
| 5,147,287 A | 9/1992 | Jewell et al. |
| 5,171,296 A | 12/1992 | Herman |
| 5,195,947 A | 3/1993 | Bode |
| 5,201,702 A | 4/1993 | Mars |
| 5,302,170 A | 4/1994 | Tweardy |
| 5,385,535 A | 1/1995 | McGuinness |
| 5,575,763 A | 11/1996 | Nagata et al. |
| 5,624,387 A | 4/1997 | McGuinness |
| 5,697,895 A | 12/1997 | Bremer |
| 5,709,649 A | 1/1998 | Chitwood |
| 5,832,926 A | 11/1998 | Towlen |
| 6,113,563 A | 9/2000 | D'Amico et al. |
| 6,267,741 B1 * | 7/2001 | Lerman ....................... 602/18 |

OTHER PUBLICATIONS

Posture Pump Neck Exerciser Professional Model Owner's Manual, pp. 1 and 2. Posture Pro, Inc.

* cited by examiner

Primary Examiner—Justine R. Yu
(74) Attorney, Agent, or Firm—Stetina Brunda Garred & Brucker

(57) ABSTRACT

A cervical remodeling collar positionable over a patient's head and neck and upon the patient's shoulders and chest for reducing forward posture of the patient's head by restoring normal forward curvature to the patient's cervical vertebrae. The collar comprises a main frame having a posterior traction member attached thereto and operative to apply a posteriorly directed force to the patient's head which draws the head into a posterior translation. Also attached to the main frame is an anterior traction member which is operative to apply an anteriorly directed force into the patient's cervical vertebrae which acts in concert with the posteriorly directed force to cause certain cervical vertebrae to be stretched into extension while other cervical vertebrae are simultaneously stretched into flexion. The posterior and anterior traction members are each adjustable so as to allow the posteriorly and anteriorly directed forces applied to the patient thereby to be selectively set to a desired level.

8 Claims, 2 Drawing Sheets

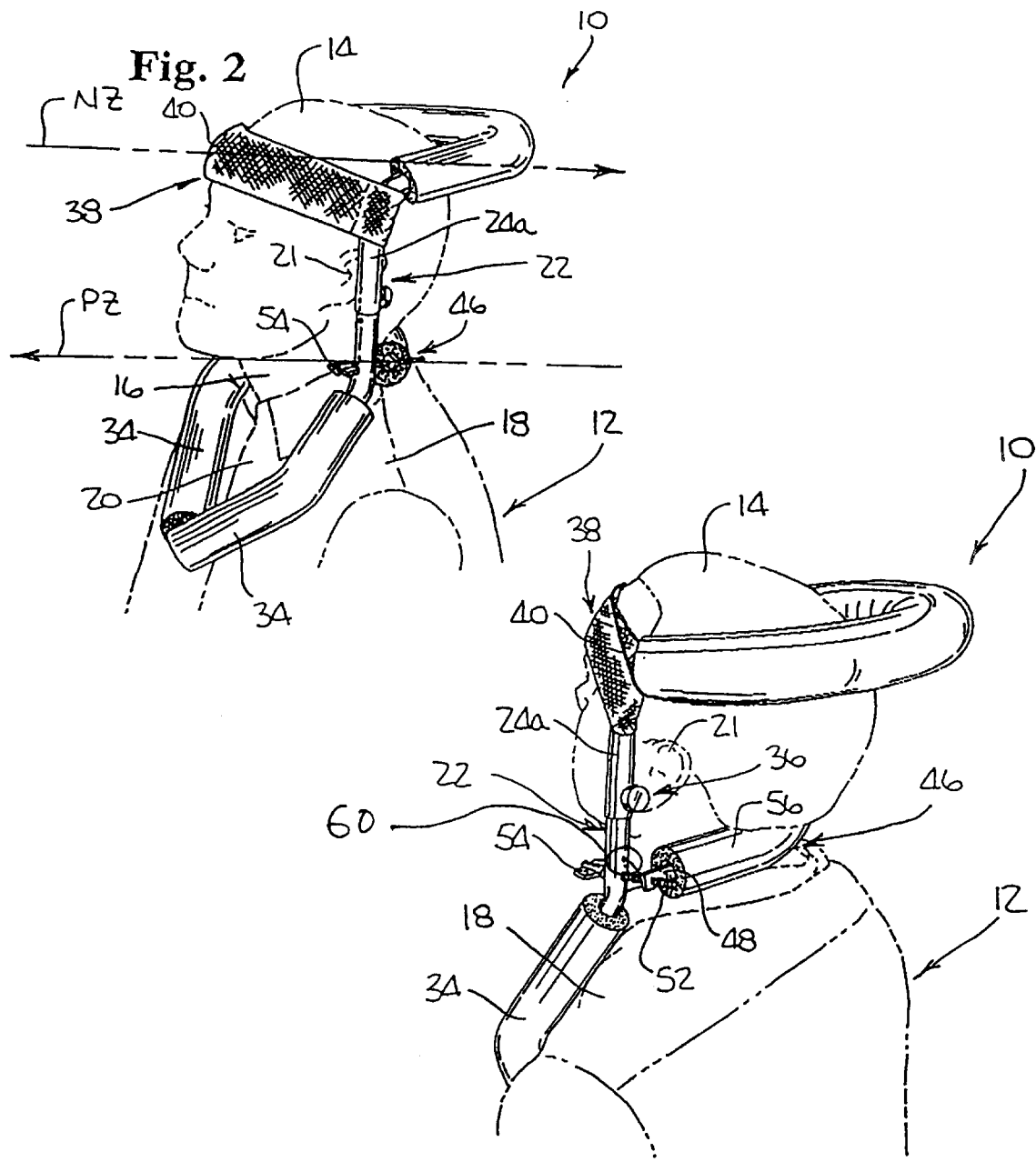

CERVICAL REMODELING COLLAR

CROSS-REFERENCE TO RELATED APPLICATIONS

This Application is a continuation of U.S. application Ser. No. 09/252,335 entitled CERVICAL REMODELING COLLAR filed Feb. 18, 1999, now abandoned, the entirety of the disclosure of which is expressly incorporated herein by reference.

STATEMENT RE: FEDERALLY SPONSORED RESEARCH/DEVELOPMENT

BACKGROUND OF THE INVENTION

The present invention relates generally to orthopedic devices such as braces, and more particularly to a traction device which is specifically adapted to restore the head, neck and thoracic's normal postural alignment by the application of dual anterior and posterior adjustable external forces.

As is well known in the medical field, a significant portion of the population suffers from a protruded or forward head posture. It has been found that chronic postural head placement forward or anterior to what is medically deemed to be physiologically neutral contributes to a wide range of adverse medical conditions, including thoracic outlet syndrome, temporomandibular joint dysfunction syndrome, dysfunctional closing pattern of the mandible, pain due to stretched muscles, adaptive muscle shortening, dorsal scapular nerve entrapment, and headaches.

The human spine consists of first through seventh cervical vertebrae, with the first cervical vertebrae being attached to the base of the scull or occiput. After the seventh cervical vertebrae, the spine transitions into the first through twelfth thoracic vertebrae, with the first thoracic vertebrae being adjacent the seventh cervical vertebrae. The thoracic vertebrae in turn transition into the first through fifth lumbar vertebrae. It has been determined that "forward head posture" is attributable to the lower cervical vertebrae being flexed in forward glide, and the upper cervical complex being extended. Stated another way, forward head posture causes the upper cervical complex to be held in a position of extension, with the lower cervical vertebrae being misaligned and often fixated in a position of flexion. This condition often occurs as a result of injury or chronic head-down or head-forward activities.

Medical study of forward head posture has revealed the effects of positive and negative Z-axis cervical translational positions upon the patient's symptoms. More particularly, it has been found that the head retraction motion, or negative Z-axis translation, causes the lower cervical vertebrae or segments to move toward an extended position, while the upper cervical vertebrae or segments become more flexed. This finding that pulling the head into a posterior translation causes flexion or kyphosis of the upper three or four cervical vertebrae has lead to the conclusion in the medical field that the head retraction motion constitutes a mirror image traction for the correction of forward head posture.

In an effort to correct forward head posture as well as misaligned lateral cervical curvatures, there has been developed in the prior art various forms of cervical extension traction which, in some cases, involve some degree of negative Z-axis translation (i.e., head retraction). However, all of these known forms of extension traction subject the upper cervical vertebrae or segments to a negative X-axis rotational force (i.e., head extension). As a result, the performance of these procedures on patients with upper cervical extension fixations does not result in optimal correction of forward head posture.

The present invention provides a wearable collar for a patient which is specifically configured to apply Z-axis translational traction to the cervical spine of the patient which, as indicated above, is a unique force related to head retraction motion that has been proven to reduce forward head posture and decrease neck pain. The present collar effectively draws the patients head into a posterior translation or head retracted posture, and then applies a secondary anterior traction into the mid-cervical vertebrae in order to restore the normal lordosis through the process of viscoelastic creep. In this respect, the Z-axis translational traction causes the sixth and seventh cervical vertebrae and first thoracic vertebrae to be stretched into extension, while the spinal region encompassing the occiput and first and second cervical vertebrae is simultaneously stretched into flexion. In addition to being able to restore the normal lordosis to the cervical spine and reduce forward head posture, the present invention is able to traction and relax the rectus capitis posterior minor muscle which has been proven to have a connective tissue link to the spinal dura matter and is widely considered a major cause of cervicogenic headaches.

Though there is also known in the prior art various cervical braces and traction devices, such prior art braces and traction devices are generally intended to support and immobilize the head and neck of a patient after injury, and not to restore the head, neck and thoracic's normal postural alignment by the application of dual anterior and posterior adjustable external forces. In this respect, though some of these prior art braces and traction devices provide either a posterior Z-axis translational force to the skull, an adjustable axial or vertical Y-axis superior directed traction to the cervical spine, or an adjustable compressive inferior directed force to the cervical spine, none of these prior art braces or traction devices provide an adjustable anterior Z-axis translational force to the mid-cervical region of the spine for purposes of remodeling the normal postural alignment and rehabilitating the normal cervical spinal lordosis. These, and other advantages associated with the present invention, will be discussed in more detail below.

BRIEF SUMMARY OF THE INVENTION

In accordance with the present invention, there is provided a collar which is wearable by a patient or user for reducing forward posture of the user's head by restoring normal forward lordosis or forward curvature to the user's cervical vertebrae. The present collar is configured to be positionable over the user's head and neck, and upon the user's shoulders and chest. In the preferred embodiment, the collar comprises a main frame including a pair of side bars having upper portions which extend in spaced, generally parallel relation to each other and lower portions. In addition to the side bars, the main frame comprises an arcuately contoured top bar which is attached to and extends between (i.e.,interconnects) the upper portions of the side bars. The arcuate configuration of the top bar causes the same to extend posteriorly about or behind the user's head when the collar is worn by the user.

The upper portions of the side bars and the top bar collectively define a top section of the main frame which is positionable over the user's head and neck. The lower portions of the side bars define a bottom section of the main frame which is positionable upon the user's chest and shoulders. In the preferred embodiment, the upper portion of each of the side bars of the main frame comprises a pair of telescoping sleeves which allows the lengths of the upper portions to be selectively increased or decreased. In this respect, the main frame further preferably comprises a locking mechanism which is cooperatively engaged to the upper portions of the side bars and operative to maintain the upper portions at prescribed lengths. The locking mechanism may comprise spring tabs which are cooperatively engaged to each of the upper portions.

In addition to the main frame, the present collar comprises a posterior traction member which is attached to the main frame, and more particularly the top section thereof. The posterior traction member is operative to apply a posteriorly directed force (i.e., a negative or posterior Z-axis translational force) to the user's head or skull which draws the head into a posterior translation or head retracted posture. The posterior traction member itself preferably comprises an elongate, flexible strap or belt having opposed ends which are attached to respective ones of the upper portions of the side bars included in the top section of the main frame. The strap itself defines an inner surface which is engagable to the user's head and includes a layer of a padded material such as neoprene disposed thereon. In addition to the inner surface, the strap defines an outer surface which has a layer of hook and loop fastener material or Velcro disposed thereon.

In addition to the posterior traction member, the present collar comprises an anterior traction member which is also attached to the top section of the main frame and operative to apply an anteriorly directed force (i.e., a positive or anterior Z-axis translational force) into the user's cervical vertebrae. This anteriorly directed force acts in concert or cooperation with the posteriorly directed force to cause certain cervical vertebrae to be stretched into extension while other cervical vertebrae are simultaneously stretched into flexion. The anterior traction member preferably comprises a flexible or rigid cervical sling member which is engagable to the back of the user's neck and movably attached to the upper portions of the side bars of the main frame. In addition to the cervical sling member, the anterior traction member comprises an adjustment mechanism which is cooperatively engaged to the cervical sling member and operative to selectively move the cervical sling member toward and away from the upper portions of the side bars, and hence the user's neck.

The cervical sling member is preferably attached to the upper portions of the side bars via a pair of externally threaded bolts, with the adjustment mechanism preferably comprising a pair of control knobs which are threadably engaged to respective ones of the bolts and positioned on the anterior side of the top section of the main frame. The rotation of the control knobs in a first direction facilitates the movement of the cervical sling member toward the upper portions of the side bars, with the rotation of the control knobs in a second direction opposite the first direction facilitating the movement of the cervical sling member away from the upper portions of the side bars. The cervical sling member is preferably covered with a layer of padding material for enhancing its comfort when engaged to the user's neck. This padding material may comprise a temperature controllable elasto-gel or other material. Additionally, it is contemplated that the cervical sling member may be provided with an inflatable air bladder which is selectively inflated via a hand-held inflator bulb.

In the present collar, the adjustability of the posterior and anterior traction members allows the posteriorly and anteriorly directed forces applied to the user thereby to be selectively set to a desired level. Additionally, the adjustability in the lengths of the upper portions of the side bars of the top section of the main frame, in cooperation with the locking mechanism, allows the posterior traction member to be maintained at a prescribed height from the anterior traction member as is needed to suit the proportions of a particular user.

Further in accordance with the present invention, there is provided a method of reducing forward head posture and restoring normal lordosis or forward curvature to a patient's cervical vertebrae through the use of the above-described collar which is wearable by the patient. The method comprises the initial step of placing the main frame of the collar upon the patient's shoulders and chest such that the anterior traction member is positioned behind the patient's neck. Thereafter, the posterior traction member is tightened across the patient's head until a posteriorly directed force of a prescribed level is applied thereto. More particularly, the tightening of the posterior traction member is preferably continued until such time as the patient's head is drawn back to a position whereat the openings of the patient's ears are located above the patient's shoulders. Finally, the anterior traction member is tightened until an anteriorly directed force of a prescribed level is directed into the back of the patient's neck. Subsequent to the tightening of the anterior traction member, the collar is preferably worn, on a repetitive basis, by the patient for anywhere from five to thirty minutes, depending on the patient's physical tolerance.

BRIEF DESCRIPTION OF THE DRAWINGS

These, as well as other features of the present invention, will become more apparent upon reference to the drawings wherein:

FIG. 2 is a front perspective view illustrating the manner in which the cervical remodeling collar shown in. FIG. 1 is worn by a patient; and FIG. 3 is a rear perspective view illustrating the manner in which the cervical remodeling collar shown in FIG. 1 is worn by a patient.

DETAILED DESCRIPTION OF THE INVENTION

Figure 1:
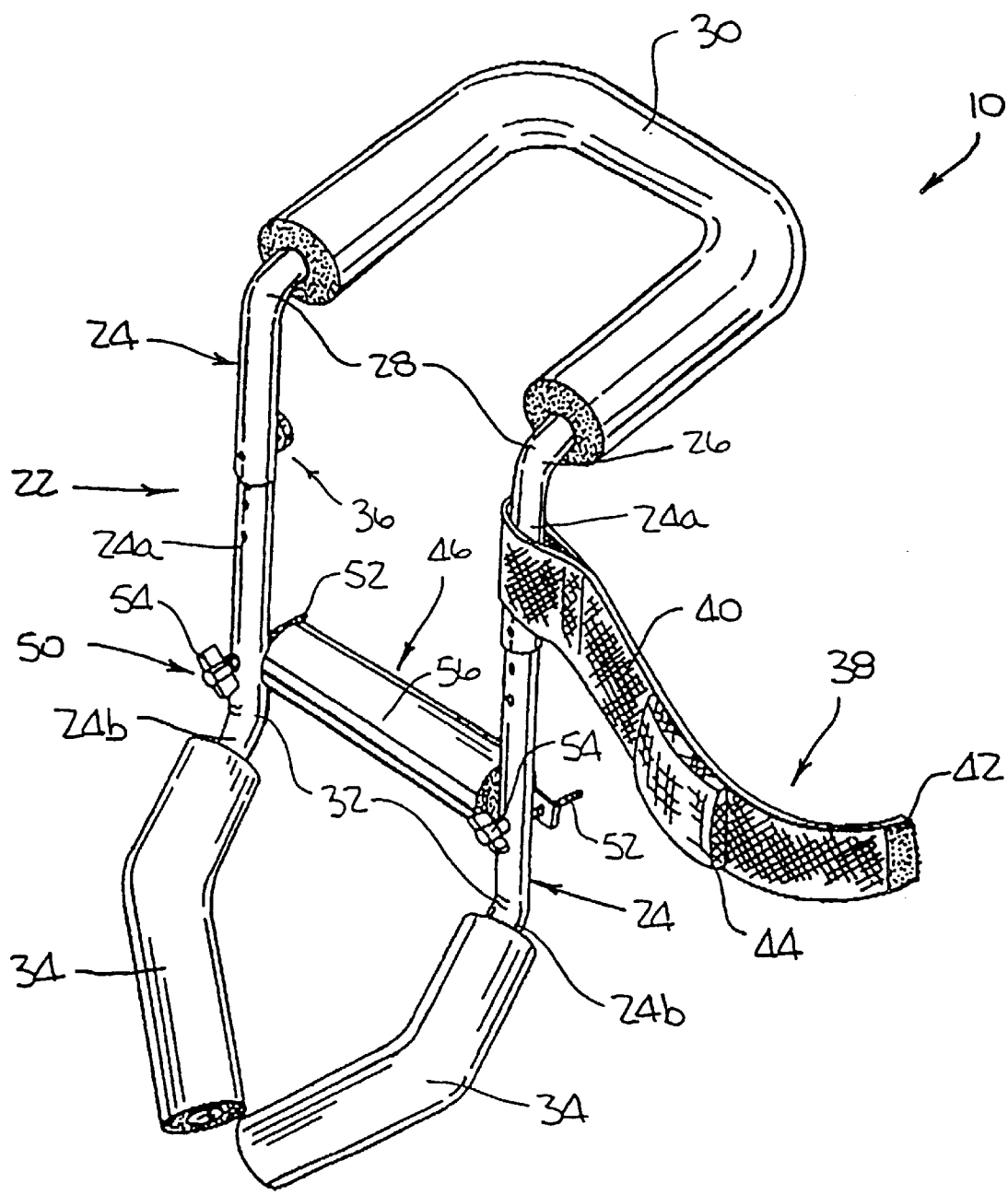
FIG. 1 is a front perspective view of the cervical remodeling collar constructed in accordance with the present invention.

Referring now the drawings wherein the showings are for purposes of illustrating a preferred embodiment of the present invention only, and not for purposes of limiting the same, FIG. 1 perspectively illustrates a cervical remodeling collar 10 which is constructed in accordance with the present invention. As will be described in more detail below with specific reference to FIGS. 2 and 3, the collar 10 is wearable by a patient 12 or other user for reducing forward posture of the head 14 of the patient 12 by restoring normal forward lordosis or forward curvature to the cervical vertebrae of the patient 12. The collar 10 is configured to be positionable over the head 14 and neck 16 of the patient 12, and upon the shoulders 18 and chest 20 of the patient 12.

In the preferred embodiment, the collar 10 comprises a main frame 22 including a middle portion defined by a pair of side bars 24 having upper portions 24*a* which extend in spaced, generally parllel relation to each other and lower portions 24*b*. In addition to the side bars 24, the main frame 22 comprises an arcuately contoured or generally U-shaped upper support or top bar 26 which is integrally connected to and extends between the upper portions 24*a* of the side bars 24. In this respect, the upper portions 24a of the side bars 24 which extended generally vertically when the collar 10 is worn by the patient 12 transition into the top bar 6 at a pair of bended regions 28 which are configured such that the top bar 26 extends at an angle in the range of from about 90 degrees to about 120 degrees relative to the posterior sides of the upper portions 24a. As seen in FIGS. 2 and 3, the arcuate or generally U-shaped configuration of the upper support or top bar 26 causes the same to extend posteriorly behind the head 14 when the collar 10 is worn by the patient 12. The top bar 26 of the main frame 22 is preferably covered by a tubular layer 30 of padded material which may be formed of foam rubber. As seen in FIG. 1, the layer 30 of padded material is sized such that the opposed ends thereof terminate approximately at respective ones of the bended regions 28.

In the collar 10, the upper portions 24a of the side bars 24 and the top bar 26 collectively define a top section of the main frame 22 which, as seen in FIGS. 2 and 3, is positionable over the head 14 and neck 16 of the patient 12. The lower portions 24b of the side bars collectively define a bottom section of the main frame 22 which, as also seen in FIGS. 2 and 3, is positionable upon the shoulders 18 and chest 20 of the patient 12. In the main frame 22, the lower portions 24b of the side bars 24 are separated from the upper portions 24a by respective ones of a pair of bended regions 32. The bended regions 32 are configured such that the lower portions 24b extend at an angle in the range of from about 130 degrees to about 155 degrees relative to the anterior sides of the upper portions 24a. Additionally, the lower portions 24b are preferably bent inwardly toward each other such that the distal ends thereof disposed furthest from the bended regions 32 terminate at locations which are substantially adjacent each other. Similar to the top bar 26, each of the lower portions 24b preferably includes a tubular layer 34 of padded material advanced thereover. The layers 34 may also be formed from foam rubber, and are preferably sized so as to extend from the distal ends of the lower portions 24b to respective ones of the bended regions 32.

As best seen in FIG. 1, the upper portion 24a of each of the side bars 24 preferably comprises a pair of telescoping sleeves which allows the lengths of the upper portions 24a to be selectively increased or decreased. In this respect, the main frame 22 further preferably comprises a locking mechanism 36 which is cooperatively engaged to the upper portions 24a and operative to maintain the same at prescribed lengths. The locking mechanism 36 may comprise spring tabs or other structures which are adapted to maintain the sleeves of the upper portions 24a in prescribed, fixed positions relative to each other.

In addition to the main frame 22, the collar 10 comprises a posterior traction member 38 which is attached to the main frame 22, and more particularly to the top section thereof. As will be discussed in more detail below, the posterior traction member 38 is operative to apply a posteriorly directed force (i.e., a negative or posterior Z-axis translational force) to the head 14 or skull which draws the head 14 into a posterior translation or head retracted posture. The posterior traction member 38 itself preferably comprises an elongate, flexible belt or strap 40 having a first end portion which is attached to one of the upper portions 24a of the side bars 24 included in the top section of the main frame 22. Such attachment is preferably facilitated by wrapping one end of the strap 40 about one of the upper portions 24a, and thereafter securing such end to the strap 40 itself through the use of Velcro or stitching or other attachment modality.

The opposite, free end of the strap 40 is releasably attachable to the upper portion 24a of the remaining side bar 24. In this respect, the strap 40 defines an outer surface which has a layer 42 of hook and loop fastener material (i.e., Velcro) disposed thereon adjacent the free end thereof. The releasable attachment of the free end of the strap 40 to the upper portion 24a of the remaining side bar 24 is facilitated by wrapping the free end about the upper portion 24a and securing the layer 42 of hook and loop fastener material to the strap 40 itself. In addition to the outer surface, the strap 40 defines an inner surface which includes a layer 44 of padded material such as neoprene disposed thereon. This layer 44 is adapted to enhance the comfort to the patient 12 when the strap 40 is extended over the forehead of the patient 12 in the manner shown in FIGS. 2 and 3.

In addition to the posterior traction member 38, the collar 10 comprises an anterior traction member 46 which is also attached to the top section of the main frame 22 and operative to apply an anteriorly directed force (i.e., a positive or anterior Z-axis translational force) into the cervical vertebrae of the patient 12. As will also be discussed in more detail below, this anteriorly directed force acts in concert or cooperation with the posteriorly directed force to cause certain cervical vertebrae of the patient 12 to be stretched into extension, while other cervical vertebrae are simultaneously stretched into flexion. The anterior traction member 46 preferably comprises a flexible or rigid cervical sling member 48 which is engagable to the back of the neck 16 of the patient 12 and movably attached to the upper portions 24a of the side bars 24 of the main frame 22. In addition to the cervical sling member 48, the anterior traction member 46 comprises an adjustment mechanism 50 which is cooperatively engaged to the cervical sling member 48 and operative to selectively move the same toward and away from the upper portions 24a of the side bars 24, and hence the neck 16 of the patient 12.

In the collar 10, the cervical sling member 48 is preferably attached to the upper portions 24a of the side bars 24 via a pair of externally threaded bolts 52. In this respect, the adjustment mechanism 50 preferably comprises a pair of control knobs 54 which are threadably engaged to respective ones of the bolts 52 and positioned on the anterior side of the top section of the main frame 22. The rotation of the control knobs 54 in a first direction facilitates the movement of the cervical sling member 48 toward the upper portions 24a of the side bars 24, with the rotation of the control knobs 54 in a second direction opposite the first direction facilitating the movement of the cervical sling member 48 away from the upper portions 24a of the side bars 24. Those of ordinary skill in the art will recognize that the control knobs 54 may alternatively be threadably engaged to the bolts 52 so as to be positioned on the posterior side of the top section of the main frame 22. The cervical sling member 48 is preferably covered with a tubular layer 56 of padded material for enhancing its comfort when engaged to the back of the neck 16 of the patient 12. This padded material may comprise a temperature controllable elasto-gel, foam rubber, or other suitable material. Additionally, though not shown, it is contemplated that the cervical sling member 48 may be provided with an inflatable air bladder which is selectively inflated via a hand-held inflator bulb.

In the collar 10 of the present invention, the adjustability of the posterior and anterior traction members 38, 46 allows the posteriorly and anteriorly directed forces applied to the patient 12 thereby to be selectively set to a desired level. Additionally, the adjustability in the lengths of the upper portions 24a of the side bars 24 of the top section of the main frame 22, in cooperation with the locking mechanism 36, allows the posterior traction member 38 to be maintained at a prescribed height from the anterior traction member 46 as is needed to suit the proportions of a particular patient 12.

Having thus described the structural attributes of the collar 10, the preferred method of using the same will now be discussed with particular reference to FIGS. 2 and 3. As indicated above, the collar 10 of the present invention is specifically adapted to reduce forward head posture and restore normal lordosis or forward curvature to the cervical vertebrae of the patient 12 when worn by the patient 12. The preferred method of using the collar 10 comprises the initial step of placing the main frame 22, and in particular the bottom section thereof defined by the lower portions 24b of the side bars 24, upon the shoulders 18 and chest 20 of the patient 12 such that the anterior traction member 46 is positioned behind the neck 16 of the patient 12. Thereafter, the posterior traction member 38 is tightened across the forehead of the patient 12 until a posteriorly directed force of a prescribed level is applied to the head 14. More particularly, the tightening of the posterior traction member 38 is preferably continued until such time as the head 14 of the patient 12 is drawn back to a position whereat the openings of the ears 21 of the patient 12 are located above the shoulders 18. Such tightening is facilitated by wrapping the free end of the strap 14 about the upper portion 24a of one of the side bars 24 in the above-described manner, and pulling on the free end prior to securing the same to the strap 14 itself via the layer 42 of hook and loop fastener material.

Subsequent to the tightening of the posterior traction member 38, the anterior traction member 46 is tightened until an anteriorly directed force of a prescribed level is directed into the back of the neck 16 of the patient 12. Such tightening of the anterior traction member 46 is facilitated by the rotation of each of the control knobs 54 of the adjustment mechanism 50 a prescribed number of turns. After the anterior traction member 46 has been properly tightened, the collar 10 is preferably worn, on a repetitive basis, by the patient 12 for anywhere from five to thirty minutes, depending on the patient's physical tolerance.

Referring now to FIG. 2, when the collar 10 is worn by the patient 12 and the posterior and anterior traction members 38, 46 properly tightened in the above-described manner, the posterior traction member 38 applies the negative or posterior Z-axis translational force labeled as NZ to the head 14 of the patient 12. At the same time, the anterior traction member 46 applies the positive or anterior Z-axis translational force labeled as PZ into the cervical vertebrae of the patient 12. Advantageously, the negative Z-axis translational force NZ applied to the head 14 by the collar 10 effectively draws the head 14 into a posterior translation or head retracted posture. The positive Z-axis translational force PZ directed into the back of the neck 16 of the patient 12, and more particularly into the mid-cervical vertebrae of the patient 12, works in conjunction with the negative Z-axis translational force NZ to restore normal lordosis through the process of viscoelastic creep. In this respect, the negative and positive Z-axis translational forces NZ, PZ, working in concert with each other, cause the sixth and seventh cervical vertebrae and first thoracic vertebrae to be stretched into extension, while the spinal region encompassing the occiput and first and second cervical vertebrae are simultaneously stretched into flexion. As such, the collar 10 provides advantages not found in prior art cervical braces and traction devices due to its ability to provide the adjustable anterior or positive Z-axis translational force PZ to the mid-cervical region of the spine of the patient 12 for purposes of remodeling the normal postural alignment and rehabilitating the normal cervical spinal lordosis.

Additional modifications and improvements of the present invention may also be apparent to those of ordinary skill in the art. Thus, the particular combination of parts and steps described and illustrated herein is intended to represent only one embodiment of the present invention, and is not intended to serve as limitations of alternative devices within the spirit and scope of the invention.

What is claimed is:

1. A collar positionable over a user's head and neck and upon the user's shoulder and chest for reducing forward posture of the user's head by restoring normal forward curvature to the user's cervical vertebrae as the user assumes an upright position, the collar comprising:

a main frame comprising:
a lower portion defining a bottom section of the main frame which is positionable upon the user's chest and shoulders, the bottom section being operative to counteract a positive anteriorly directed force directed about a z-axis relative the user's neck;
a pair of approximately vertically disposed side bars wherein each side bar defines an upper portion, such that the upper portions extend in spaced, generally parallel relation to each other, and wherein each side bar defines a lower portion attached to the respective upper portions such that the lower portions can be positioned upon the user's shoulder and chest;
a top bar attached to and extending between the upper portions of the side bars, the top bar being configured to extend behind the user's head when the collar is worn by the user;
the upper portions and the top bar collectively defining a top section of the main frame which is positionable over the user's head and neck and has the posterior and anterior traction members attached thereto;
a posterior traction member attached to the upper portions of the main frame and operating in concert with the bottom section to apply a negative posteriorly directed force about the z-axis relative the user's head which draws the head into a posterior translation;
an anterior traction member attached to the upper portions of the main frame and operative to apply a positive anteriorly directed force about the z-axis into the user's cervical vertebrae in simultaneously opposing the posteriorly directed force to cause certain cervical vertebrae to be stretched into extension while remaining cervical vertebrae are simultaneously stretched into flexion; and
the posterior and the anterior traction members are selectively adjustable to engage the user's head and neck respectively so as to allow the posteriorly and anteriorly directed forces applied to the user thereby to be selectively set to a desired level for traction and reestablishing normal postural relationship of the skull and the body from lateral view.

2. The collar of claim 1 wherein the posterior traction member comprises an elongate, flexible strap having opposed ends which are attached to respective ones of the upper portions of the side bars of the main frame.

3. The collar of claim 2 wherein the strap defines an inner surface which is engageable to the user's head and includes a layer of padded material disposed thereon and an outer surface having a layer of hook and loop fastener material disposed thereon.

4. The collar of claim 1 wherein the anterior traction member comprises:

a cervical sling member which is engageable to the user's neck and movably attached to the upper portions of the side bars of the main frame; and an adjustment mechanism which is cooperatively engaged to the cervical sling member and operative to selectively move the cervical sling member toward and away from the upper portions of the side bars.

5. The collar of claim 4 wherein:

the cervical sling member is attached to the upper portions of the side bars via a pair of externally threaded bolts;

the adjustment mechanism comprises a pair of control knobs which are rotatably engaged to respective ones of the bolts; and the rotation of the control knobs in a first direction facilitating the movement of the cervical sling member toward the upper portions, with the rotation of the control knobs in a second direction opposite the first direction facilitating the movement of the cervical sling member away from the upper portions.

6. The collar of claim 4 wherein the cervical sling member includes a layer of padding material disposed thereon.

7. The collar of claim 1 wherein:

each of the upper portions comprises a pair of telescoping sleeves which allows for a selective adjustment in the length thereof; and the main frame further comprises a locking mechanism which is cooperatively engaged to the upper portions and operative to maintain the upper portions at prescribed lengths.

8. A collar positionable over a user's head and neck and upon a user's shoulders and chest for reducing forward posture of the user's head by restoring normal forward curvature to the user's cervical vertebrae, the collar comprising:

a main frame comprising an upper U-shaped support;

a middle portion comprising two parallel bars which are at approximately a right angle to the upper support;

a strap attached to the upper support;

a lower support consisting of two bars bent towards each other and attached to the middle portion at a approximately a 30 degree angle relative to the middle portion;

a cross member extending between the two parallel bars, the cross member being positionable at variable vertical locations along the two parallel bars, the cross member being positionable at variable vertical locations along the two parallel bars; and the strap providing horizontal posterior force to the skull while the cross member simultaneously provide an opposing negative anteriorly directed force about a z-axis to the cervical spine.

\* \* \* \* \*